United States Patent [19]
Horiuchi et al.

[11] Patent Number: 5,270,212
[45] Date of Patent: Dec. 14, 1993

[54] CELL ANALYSIS APPARATUS

[75] Inventors: Hideyuki Horiuchi, Abiko; Shinichi Sakuraba, Katsuta; Toshio Kaneko, Katsuta; Nobuyuki Tatara, Katsuta; Ryohei Yabe, Katsuta; Hiroshi Ohki, Tsuchiura; Isao Yamazaki, Ibaraki, all of Japan; Ryo Miyake, Enschede, Netherlands

[73] Assignees: Hitachi, Ltd., Tokyo; Hitachi Instrument Engineering Co., Ltd., Katsuta, both of Japan

[21] Appl. No.: 841,487

[22] Filed: Feb. 26, 1992

[30] Foreign Application Priority Data

Mar. 20, 1991 [JP] Japan .................. 3-056355

[51] Int. Cl.⁵ .................................... G01N 35/00
[52] U.S. Cl. .................................... 436/45; 436/63;
422/63; 422/64; 422/82.08; 422/103; 435/289;
435/291; 435/312; 435/316; 73/61.59;
73/863.73; 73/864.83; 73/864.84; 356/39;
356/244
[58] Field of Search ........... 435/291, 289, 290, 312,
435/316, 317.1; 422/63, 64, 82.02, 82.05, 82.08,
103; 436/43, 45, 63; 73/864.83, 864.84, 61.59,
64.56, 863.73; 356/39, 244

[56] References Cited

U.S. PATENT DOCUMENTS

| | | | |
|---|---|---|---|
| 3,964,513 | 6/1976 | Molner | 73/864.83 X |
| 3,971,630 | 7/1976 | Sandrock et al. | 422/64 X |
| 3,991,055 | 11/1976 | Godin et al. | 73/864.84 X |
| 4,030,888 | 6/1977 | Yamamoto et al. | 23/253 R |
| 4,152,391 | 5/1979 | Cabrera | 73/864.83 X |
| 4,186,187 | 1/1980 | Jahnsen et al. | 422/64 |
| 4,221,568 | 9/1980 | Boettger | 422/64 X |
| 4,254,084 | 3/1981 | Blum | 435/291 X |
| 4,359,447 | 11/1982 | Welch | 422/64 X |
| 4,607,526 | 8/1986 | Bachenheimer et al. | 73/432 PS |
| 4,706,207 | 11/1987 | Hennessy et al. | 364/555 |
| 4,726,237 | 2/1988 | Yung | 73/864.83 |
| 4,729,876 | 3/1988 | Hennessy et al. | 422/103 |
| 4,928,539 | 5/1990 | Champseix et al. | 422/64 X |
| 4,948,565 | 8/1990 | Bemis et al. | 422/103 |
| 4,957,008 | 9/1990 | Proni et al. | 73/864.83 |
| 5,079,959 | 1/1992 | Miyake et al. | 73/864.85 |

*Primary Examiner*—James C. Housel
*Assistant Examiner*—Maureen M. Wallenhorst
*Attorney, Agent, or Firm*—Fay, Sharpe, Beall, Fagan, Minnich & McKee

[57] ABSTRACT

This invention relates to an apparatus for analyzing cells in a biological liquid sample, such as blood, in which apparatus a flow passage in a sample pretreatment system can be shortened with a simple construction. A sample metering chamber, a mixing chamber and a measurement liquid extracting chamber are formed in a rotary sliding member of a pretreatment portion. The rotary sliding member is intermittently rotated so as to shift a sample from one chamber to another to perform a necessary treatment. Fluorescence or scattering light with respect to the sample, mixed with a reagent in the pretreatment portion, is detected by a flow cell.

14 Claims, 15 Drawing Sheets

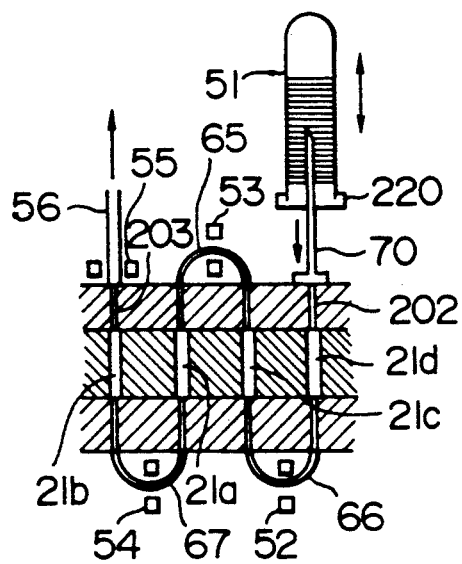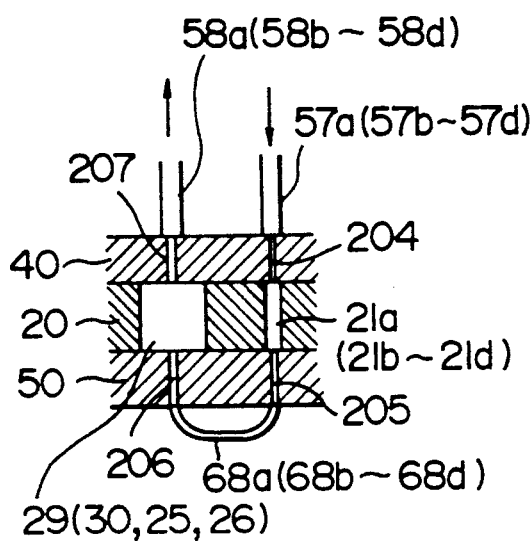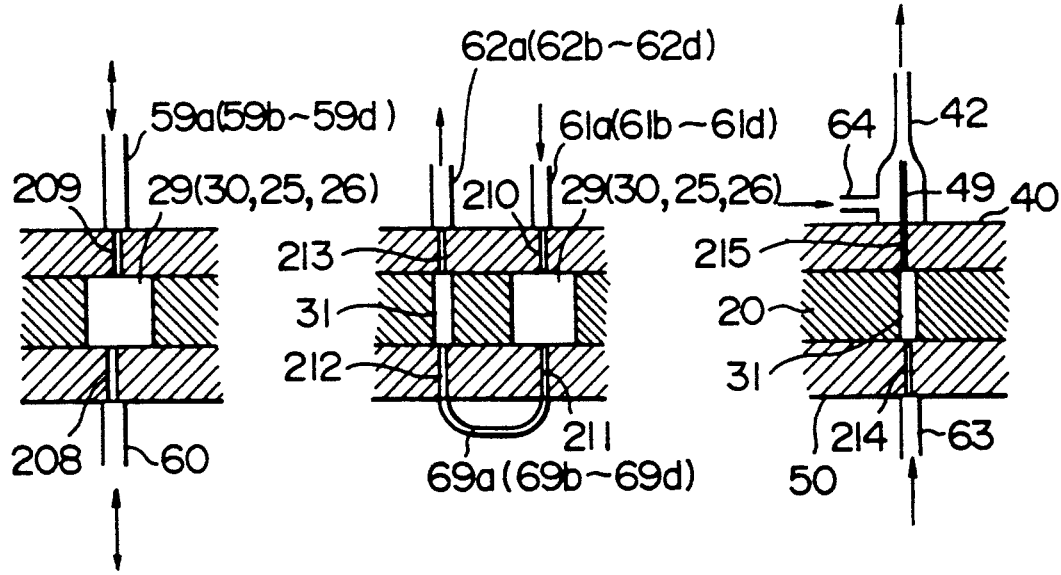

FIG. 18A
FIG. 18B
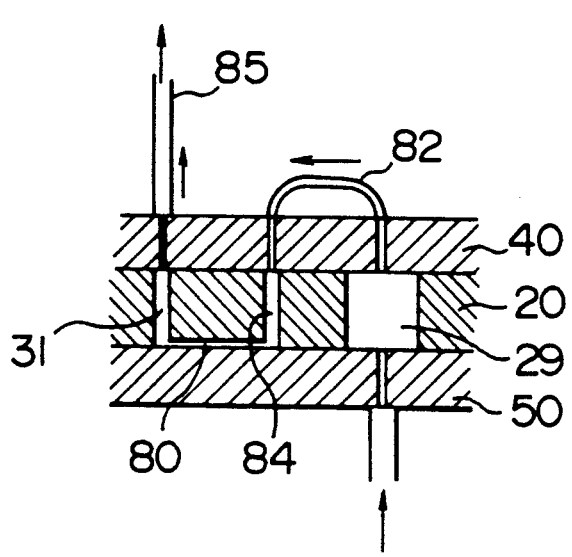
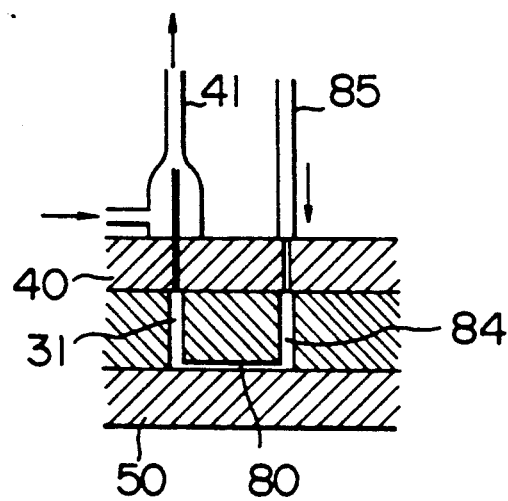
FIG. 19
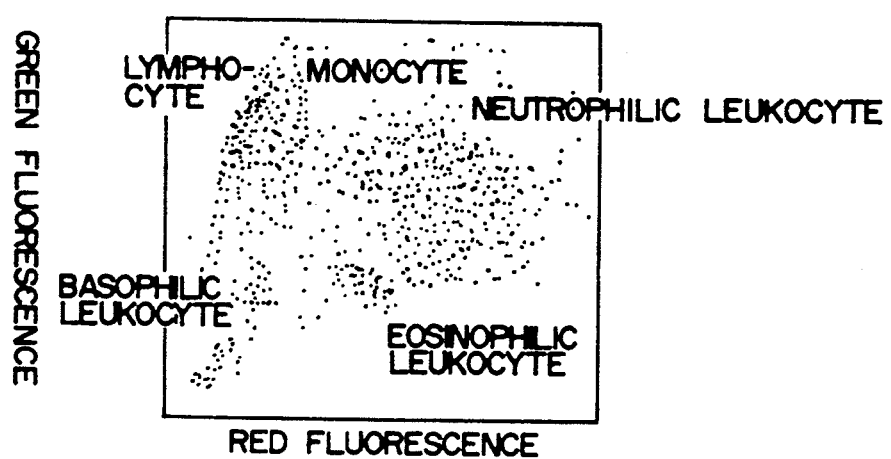

CELL ANALYSIS APPARATUS

BACKGROUND OF THE INVENTION

This invention relates generally to a cell analysis apparatus, and more particularly to a cell analysis apparatus of the type which is suited for analyzing cells in a biological liquid sample, such as blood, after staining the cells.

One known method of classifying and analyzing cells (e.g. blood corpuscles) in a blood sample or counting the cells in terms of particles uses a sheath flow cell. A first publication describing an analysis method of this type is Japanese Patent Publication No. 59-853(B). This publication describes a method in which leukocytes (white corpuscles) are stained with acridine orange, and a sample containing the staining agent and the leukocytes is caused to flow through a sheath flow cell. A laser beam is then applied to the sheath flow cell, and the fluorescence of the leukocytes is detected so as to classify the leukocytes.

A second publication describing the use of a sheath flow cell is Japanese Patent Laid-Open No. 59-228147(A). This second publication describes a blood corpuscle counter in which blood corpuscle-suspended liquid is caused to flow through the sheath flow cell, and a laser beam is applied to the sheath flow cell. The forward-scattering light is then detected so as to find the number of the blood corpuscles and the distribution of the particles.

This second publication describes a pretreatment for diluting the blood sample. More specifically, a predetermined amount of the blood sample, introduced from a sample vessel via a nozzle, is metered by a first flow switch valve, and then is fed to a dilution vessel having on-off valves at its upper and lower portions, where the blood sample is diluted. Thereafter, the diluted sample is metered by a second flow switch valve, and is caused to flow through the sheath flow cell so that the number of the blood corpuscles can be counted.

A third publication describing the use of a sheath flow cell is Japanese Patent Laid-Open No. 2-80937(A). This third publication describes an analysis apparatus in which a number of sample cups are successively located at a sample suction position, and a sample in the sample cup is fed to the sheath flow cell by a pipet nozzle, where scattering light or fluorescence of the leukocyte is detected. The pretreated blood sample is contained in the sample cup, and the blood corpuscle-containing sample in the sample cup is drawn by the pipet nozzle.

In the above Japanese Patent Publication No. 59-853(B), although the conditions of the staining of the leukocytes are described in detail, no consideration is given at all to an apparatus for automating the staining treatment. When measuring the blood corpuscle cells, pretreatments, such as dilution, staining and hemolysis, are needed. Similarly, the above third publication also gives no consideration to the automation of the pretreatments.

In the above Japanese Patent Laid-Open No. 59-228147(A), although the dilution of the blood sample is automated, the number of the component parts is large, so that the flow passage system is long. Therefore, the analysis apparatus is of a large size, and it takes much time to wash the flow passage system. In addition, in this technique, the two flow switch valves provided between the sample vessel and the flow cell have the sole function of metering the sample.

SUMMARY OF THE INVENTION

It is an object of this invention to provide a cell analysis apparatus in which a flow passage of a pretreatment system can be shortened with a simple construction.

Another object of the invention is to provide a cell analysis apparatus in which, despite the fact that a pretreatment system can be of a smaller size, mutual contamination between samples can be reduced.

A further object of the invention is to provide a cell analysis apparatus in which a blood corpuscle classifying measurement and a blood corpuscle counting measurement can be performed with one sampling.

A cell analysis apparatus according to the present invention comprises a rotary sliding member having a sample metering chamber and a mixing chamber, and a fixed portion arranged in such a manner that its sliding surface faces the rotary sliding member. A sample introducing port, a treatment liquid introducing port, an agitating port, etc., are formed in the fixed portion. Devices for effecting the intended treatments are connected to these ports, respectively. Cells in the sample in the mixing chamber are subjected to a staining treatment, a hemolysis treatment or a dilution treatment by a treatment liquid. Then, the sample liquid is shifted from the rotary sliding member to a flow cell, and is measured by detection means.

In a preferred form of the invention, washing liquid flow grooves are formed in the sliding surface of the fixed portion facing the rotary sliding member. In another preferred form of the invention, the cell staining treatment and the cell hemolysis treatment are carried out separately from each other in the rotary sliding member, and these cells are measured by corresponding flow cells, respectively.

In the present invention, the sample metering chamber and the mixing chamber are formed in the rotary sliding member, the various connection ports are formed in the fixed portion, and the rotary sliding member is intermittently rotated by a predetermined angle. With this construction, the mixing of the sample with the treatment liquid such as the staining treatment liquid, as well as the treatment such as the staining treatment, are effected in the flow passage switching means. The cell-containing sample collected in the sample metering chamber, as well as the treatment liquid from the treatment liquid supply device, are introduced into the mixing chamber. Since the mixing chamber is greater in volume than the sample metering chamber, the mixing of the two liquids can be carried out smoothly.

The sample is treated while being shifted from one chamber of the rotary sliding member to another via the fixed portion, and therefore the length of the flow passage can be shortened. Further, since the sample pretreatment means is constituted by the rotary sliding member and the fixed portion, the construction of the pretreatment system can be greatly simplified.

The washing liquid flow grooves are formed in the sliding surface of the fixed portion, and a washing liquid is caused to flow through these grooves, thereby removing a very small amount of the sample leaking to the sliding surface of the rotary sliding member. Therefore, the sliding surface is cleaned, and the possibility of contamination of the subsequent sample with the residual preceding sample can be reduced. The various chambers in the rotary sliding member can be washed by the washing liquid after the sample treatments are finished.

A plurality of sample metering chambers communicate with one another so as to extract the blood corpuscle cell sample, and the sample metering chambers communicate respectively with their corresponding mixing chambers so as to feed the sample thereto. Further blood corpuscle-containing liquids in the mixing chambers are fed respectively to different flow cells. With this arrangement, the blood corpuscle classification measurement and the blood corpuscle counting measurement can be effected with one sampling.

BRIEF DESCRIPTION OF THE DRAWINGS

FIGS. 5A to 5E are views showing the pretreatment operation of a blood sample;

FIGS. 18A and 18B are cross-sectional views showing a modified measurement liquid extracting chamber;

FIG. 19 is a view showing an example of the leukocyte classification obtained by the present invention;

DESCRIPTION OF THE PREFERRED EMBODIMENTS

A first embodiment of the present invention will now be described with reference to FIGS. 1 and 12.

Figure 1:
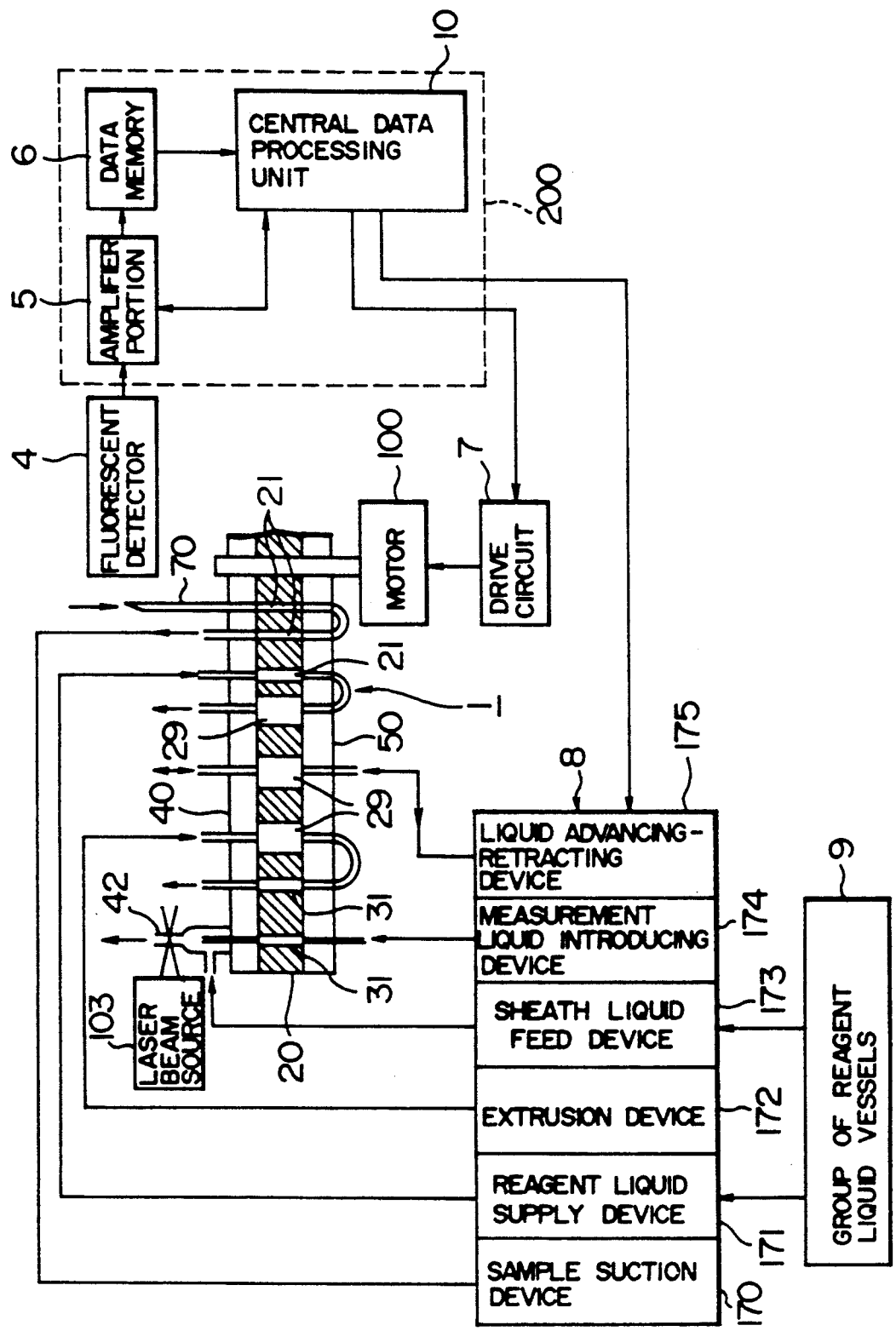
FIG. 1 is a schematic view of an overall construction of a first embodiment of the invention.

FIG. 1 is a schematic view of the overall construction of a blood corpuscle cell analysis apparatus embodying the present invention. A blood sample containing blood corpuscles is introduced into a pretreatment portion 1 via a piercing needle 70 serving as a sample introducing pipe. The pretreatment portion 1 comprises a rotary sliding member 20 intermittently rotated a predetermined angle by a drive motor 100, and a pair of upper and lower fixed portions 40 and 50 which support the rotary sliding member 20 therebetween and are fixedly mounted. A sample metering chamber 21, a mixing chamber 29 and a measurement liquid extracting chamber 31 are formed in the rotary sliding member 20.

The blood sample that is metered and extracted at the sample metering chamber 21 is fed to the mixing chamber 29 in the rotary sliding member 20 in accordance with the flow switching operation of the pretreatment portion 1, and then is fed to the measurement liquid extracting chamber 31. For introducing the blood sample into the sample metering chamber 21, a sample suction device 170 (which has a pump mechanism of an ordinary syringe-type) of a multi-mechanism portion 8 is operated. For introducing the blood sample into the mixing chamber 29 from the sample metering chamber 21 and for introducing a staining liquid into the mixing chamber 29, a reagent liquid supply device 171 (which has a syringe mechanism) of the multi-mechanism portion 8 is operated.

The staining liquid to be supplied is held in a group of reagent liquid vessels 9. For mixing the blood sample with the staining liquid in the mixing chamber 29, a liquid advancing-retracting device 175 (which has a syringe pump for moving the liquid in the mixing chamber 29 back and forth) of the multi-mechanism portion 8 is operated. For shifting the mixture liquid from the mixing chamber 29 to the measurement liquid extracting chamber 31 after the blood corpuscles in the blood sample begin to be stained, an extrusion device 172 (which has a syringe mechanism) of the multi-mechanism portion 8 is operated. For shifting the measurement liquid (which contains a staining agent and the cells), collected in the measurement liquid extracting chamber 31, to a flow cell 42, a measurement liquid introducing device 174 (which has a syringe mechanism) of the multi-mechanism portion 8 is operated.

A sheath liquid is supplied to the flow cell 42 by a sheath liquid feed device 173. The sheath liquid is held in the group of reagent liquid vessels 9. The operation of each of the devices of the multi-mechanism portion 8, as well as the operation of a motor drive circuit 7, is controlled by a central data processing unit 10.

A measurement portion for measuring information based on the cells flowing through the sheath flow cell 42 comprises the sheath flow cell 42, a laser beam source 103, and a fluorescence detector 4. A signal processing portion 200 for data-processing the detected cell information comprises an amplifier portion 5, a data memory 6, and the above central data processing unit 10 for computing and analyzing purposes. The amplifier portion 5 includes an amplifier, a discriminator, a peak hold circuit, an analog-to-digital converter, and so on. The central data processing unit 10 analyzes data (which include the decision of the name of the blood corpuscles, the counting of the blood corpuscles, the judgment of abnormal blood corpuscles, the classification of the blood corpuscles, a differential ratio, a distribution pattern, and a histogram) necessary for examination and diagnosis, and outputs results.

Although only the staining treatment is shown in the pretreatment portion 1 in FIG. 1 for the sake of simplicity of the illustration, a hemolysis treatment chamber 25 for mixing the blood corpuscle sample with a hemolysis agent-containing liquid, as well as a dilution chamber 26 for mixing the blood sample with the dilution liquid, is formed in the rotary sliding member 20, as described later with reference to FIG. 2. In FIG. 1, although a plurality of chambers designated by the same reference numerals are shown with respect to each of the sample metering chamber 21, the mixing chamber 29 and the measurement liquid extracting chamber 31, these are provided merely for explanation purposes, and actually, each of the three chambers 21, 29 and 31 is only one.

Figure 3:
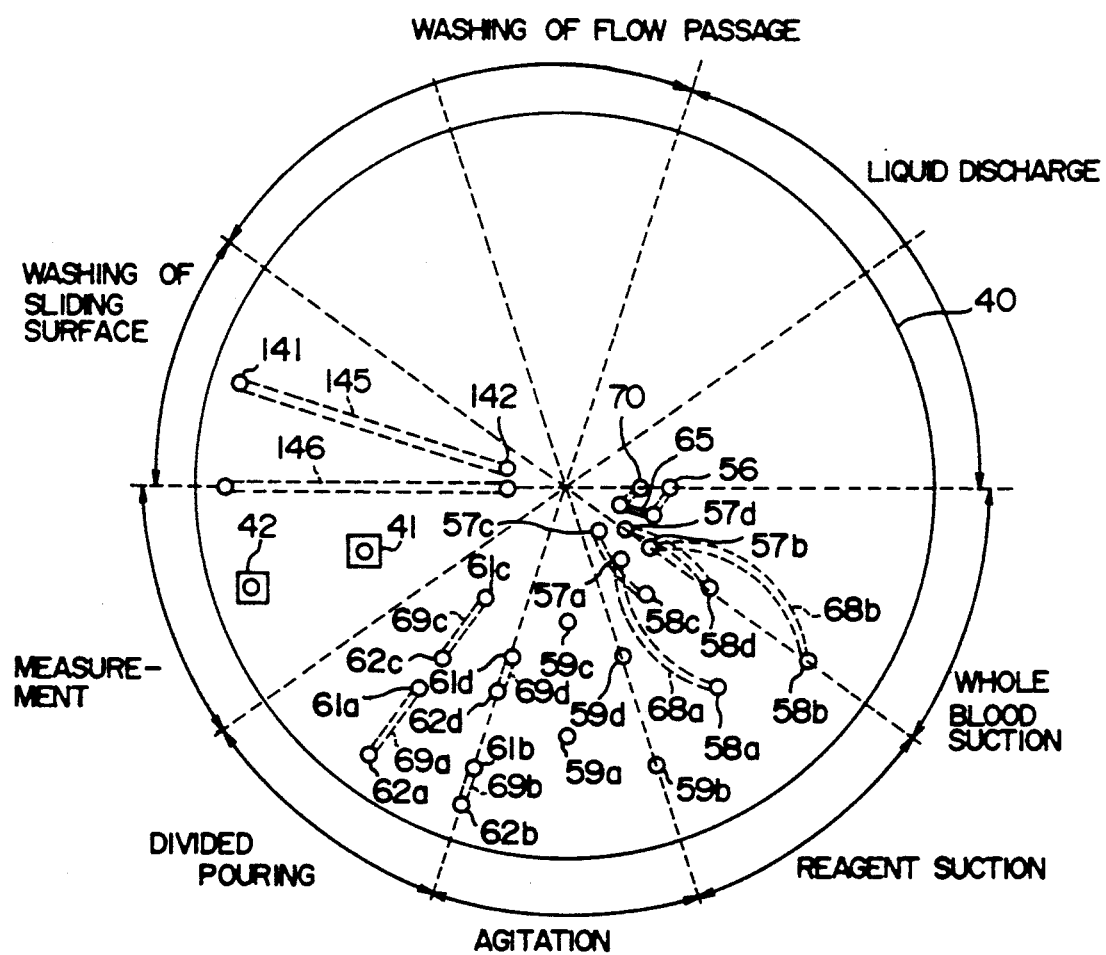
FIG. 3 is an explanatory view of an upper fixed portion of the apparatus of FIG. 1.
Figure 4:
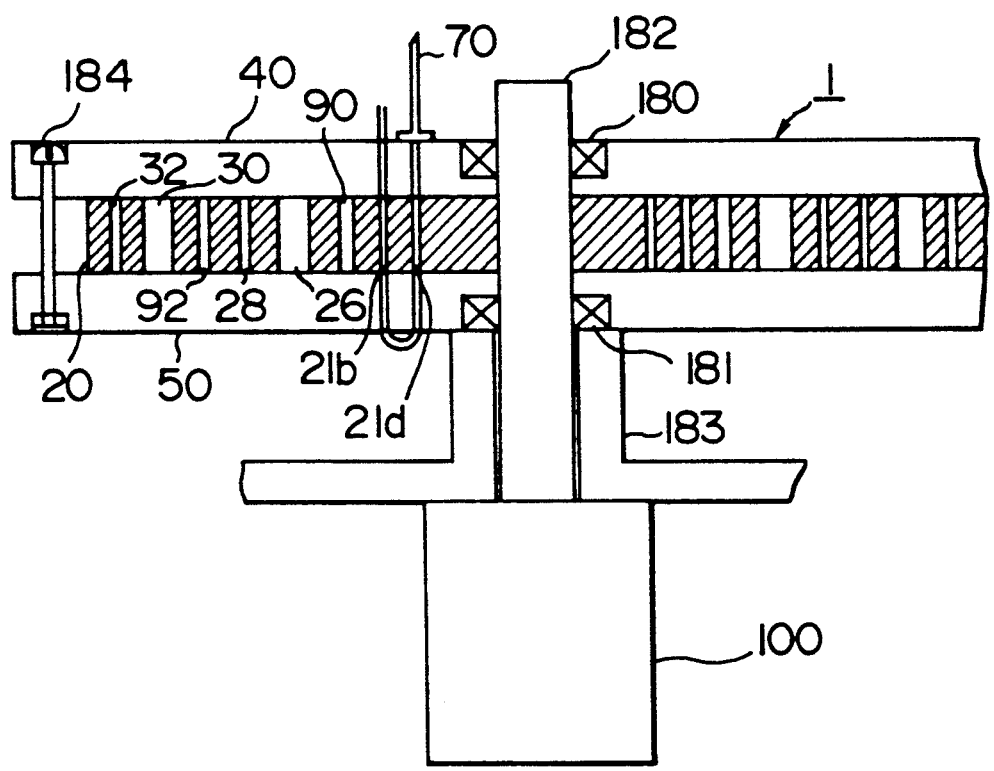
FIG. 4 is a cross-sectional view of a portion of a pretreatment portion of the first embodiment.

The construction of the pretreatment portion 1 of FIG. 1 will now be described with reference to FIGS. 2 to 5E. FIG. 2 shows the rotary sliding member 20, FIG. 3 shows the fixed portion 40, and FIG. 4 shows a cross-section of a portion of the pretreatment portion 1. FIG. 5 shows the operation, and more specifically, FIGS. 5A to 5E show a whole blood suction arrangement, a reagent suction arrangement, an agitation arrangement, a divided pouring arrangement, and a measurement, respectively.

As shown in FIG. 3, the fixed portion 40 of the pretreatment portion 1 is imaginarily divided into ten segments of the same angle, and each segment is handled so as to effect four kinds of treatments i.e., the staining for classifying the leukocytes, the staining for classifying reticulocytes, the hemolysis for counting the leukocytes, and the dilution for counting the erythrocytes per specimen. Each segment has a region having an angle of 36°.

Figure 2:
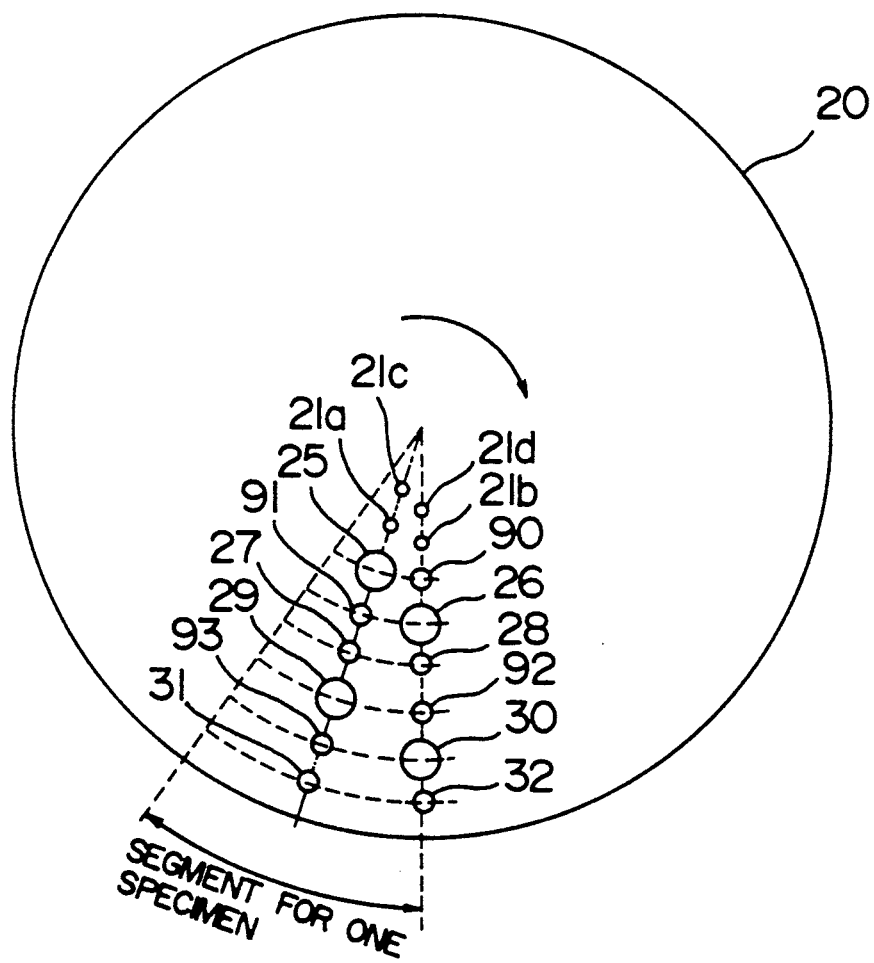
FIG. 2 is an explanatory view of a rotary sliding member of the apparatus of FIG. 1.

In FIG. 2, with respect to the sliding rotary member 20, there are shown the treatment chambers of the four lines formed in one segment for one specimen. A plurality of similar treatment chamber lines are formed in the rotary sliding member 20 so that a plurality of specimens can be treated in a parallel manner.

A pair of sample metering chambers 21a and 21c, 21b and 21d; a pair of mixing chambers 25 and 29; 26 and 30; a pair of measurement liquid extracting chambers 27 and 31, 28 and 32; and a pair of washing holes 91 and 93, 90 and 92 (provided radially outwardly of the respective chambers) are arranged in two lines in the rotary sliding member 20 in the same radial direction of this rotary sliding member. As shown in FIG. 4, the rotary sliding member 20 is mounted on a rotation shaft 182, and the rotation shaft 182 is intermittently rotated clockwise by the drive motor 100 by an angle corresponding to a half of one segment, as indicated by an arrow in FIG. 2. The fixed portions 40 and 50 have rotation bearings 180 and 181, respectively, which are in contact with the rotation shaft 182. The upper fixed portion 40 and the lower fixed portion 50 are connected together by screws 184. The lower fixed portion 50 and the motor 100 are fixedly mounted on a base 183.

The four kinds of mixing chambers 25, 26, 29 and 30 are formed in the rotary sliding member 20. The volume of the mixing chambers 25, 26, 29 and 30 is larger than the volume of the sample metering chambers 21a to 21d and the volume of the measurement liquid extracting chambers 27, 28, 31 and 32.

In this embodiment, for each specimen, there are provided the function of staining leukocytes so as to detect fluorescence to classify the leukocytes, the function of staining reticulocytes so as to detect fluorescence to classify the reticulocytes, the function of subjecting erythrocytes to a hemolysis treatment so as to count the leukocytes by electrical resistivity, and the function of diluting the blood sample so as to count erythrocytes by electrical resistivity. The mixing chambers 29, 30, 25 and 26 are 26 are therefore provided so as to correspond to these four treatment channels, respectively. Thus, the chamber 29 constitutes the leuko-cyte-classifying staining chamber, the chamber 30 constitutes the reticulocyte staining chamber, the chamber 25 constitutes the leukocyte-counting hemolysis chamber, and the chamber 26 constitutes the erythrocyte-counting diluting chamber 26.

The measurement liquid from the leukocyte-classifying staining chamber 29 and the reticulocyte staining chamber 30 among the mixing chambers is led to the flow cell 42, so that the fluorescence is detected. The measurement liquid from the leukocyte-counting hemolysis chamber 25 and the erythrocyte-counting dilution chamber 26 among the mixing chambers is led to another flow cell 41, so that the electrical resistivity is measured. The rotary sliding member 20 makes one rotation by 20 steps.

Next, the process step regions will be described with reference to FIGS. 2, 3 and 5A to 5E.

When the segment for one specimen shown in FIG. 2 is in the whole blood suction step region shown in FIG. 3, the sample metering chamber 21d is in registry with the sample introducing port 202, as shown in FIG. 5A, and the piercing needle 70 is attached to this port 202. The sample metering chamber 21b disposed closer to the outer periphery is in registry with a port 203, and a suction port 56 connected to the sample suction device 170 (FIG. 1) is also connected to port 203. The sample metering chambers 21c and 21a communicate with each other via a connecting pipe 65.

When the rotary sliding member 20 is rotated in the direction of the arrow shown in FIG. 2 to bring the illustrated segment for one specimen to a reagent suction step region shown in FIG. 3, reagent discharge ports 57a to 57d communicating with the respective reagent liquid supply devices 171 are connected respectively to their corresponding introducing ports 204, as shown in FIG. 5B, and are communicatable respectively with discharge pipes 58a to 58d (which are connected respectively to their corresponding ports 207) via respective connecting pipes 68a to 68d connecting outlet ports 205 of the metering chambers respectively to inlet ports 206 of the staining chambers.

When the rotary sliding member 20 is further rotated to bring the specimen segment into registry with an agitating step region, discharge pipes 60 communicating with the respective liquid advancing-retracting devices 175 are connected to agitating port 208, as shown in FIG. 5C. Mixture liquid releasing pipes 59a to 59d each having an upper portion open to the atmosphere are connected respectively to ports 209 formed in the upper fixed portion 40.

In a divided pouring step region, extrusion liquid introducing pipes 61a to 61d are connected respectively to ports 210 in the upper fixed portion 40, as shown in FIG. 5D, and discharge pipes 62a to 62d leading to a drain are connected respectively to ports 213. Each of the extrusion liquid introducing pipes 61a to 61d communicates with the extrusion device 172. Mixture liquid outlet ports 211 in the lower fixed portion 50 communicate respectively with mixture liquid inlet ports 212 via respective connecting pipes 69a to 69d.

In a measurement step region, the two sheath flow cells 41 and 42 are connected to the upper fixed portion 40 as shown in FIG. 3. An extrusion port 214 in the lower fixed portion 50 is connected to a solution discharge port 63 communicating with the measurement liquid introducing device 174. Here, as shown in FIG. 5E, the measurement liquid extracting chamber 31 communicates with the extrusion port 214 in the lower fixed portion 50 and also with a measurement liquid extracting port 215 connected to the upper flow cell 42. The flow cell 42 has a sample discharge portion 49 and a sheath liquid inflow portion 64, and the sheath liquid from the sheath liquid feed device 173 is introduced into the flow cell 42, flowing in such a manner as to sheath the sample, which flows from the discharge portion 49 via the measurement liquid extracting port 215.

Figure 9:
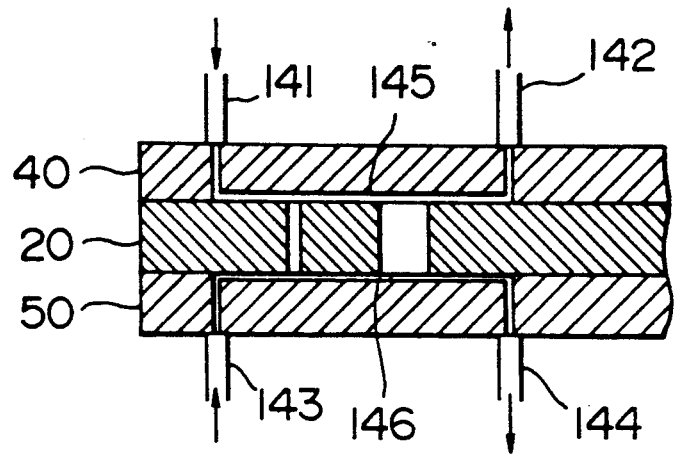
FIG. 9 is an explanatory view of sliding surface-washing grooves in the first embodiment.

As shown in FIGS. 3 and 9, washing grooves 145 and 146 are formed respectively in the sliding surfaces of the fixed portions 40 and 50. The washing grooves 145 and 146 are open toward the upper and lower sliding surfaces of the rotary sliding member 20, respectively, and washing liquids, flowing respectively into these grooves from their corresponding washing liquid inlets 141 and 143, are discharged respectively from discharge ports 142 and 144. By providing a plurality of such washing liquid flow grooves 145 and a plurality of such washing liquid flow grooves 146 respectively in those portions of the sliding surfaces of the fixed portions 40 and 50 extending from the measurement liquid extracting port 215 to the sample introducing port 202, the sliding surfaces are cleaned more effectively.

In the course of a long time, the blood sample, the staining liquid, etc., penetrate little by little into the sliding surfaces of the rotary sliding member 20; however, by the provision of the washing liquid flow grooves, the sliding surfaces of the rotary sliding member 20 are cleaned in accordance with the rotational movement of this member 20.

In a flow passage washing step region in FIG. 3, the flow passages in the pretreatment portion 1 are washed by the washing liquid. In a liquid discharge step region in FIG. 3, compressed air is fed into the flow passages in the pretreatment portion 1 to discharge the liquid from the flow passages, thereby preparing for the next whole blood introduction.

Figure 6:
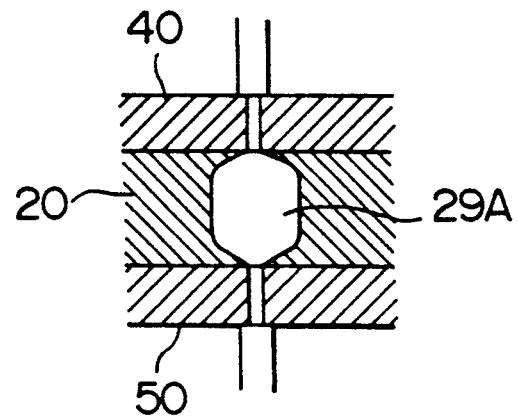
FIG. 6 is a cross-sectional view showing a modified mixing chamber for mixing the sample with a reagent.

Although the mixing chambers 25, 26, 29 and 30 (which are formed in the rotary sliding member 20) shown in FIGS. 1 and 5A to 5E have a cylindrical shape, each of them may be replaced by a mixing chamber having a curved inner peripheral surface as designated at 29A in FIG. 6.

The operation of the pretreatment portion 1 will now be described with reference to FIGS. 1 to FIG. 5E. Each of the whole blood suction step, the reagent suction step, the agitating step, the divided pouring step and the measurement step is carried out by two steps.

(a) Whole blood suction step

The whole blood sample containing the blood corpuscles is held in a blood thief tube 51 shown in FIG. 5A, and this blood thief tube 51 is sealed by a rubber cap 220. The distal end of the piercing needle 70 is cut to provide a sharp edge. An air hole (not shown) is formed in the needle 70 to facilitate the introduction of the sample into the pretreatment portion.

The blood thief tube 51 is attached from above in such a manner that the piercing needle 70 passes through the cap 220. Then, the sample suction device 170 is operated. As a result, the blood sample is fed via the connecting pipes 66, 65 and 67, and is filled in the four sample metering chambers 21d, 21c, 21a and 21b. Then, the sample suction device 170 is stopped, and the rotary sliding member 20 is rotated by one step, and the blood thief tube 51 is moved upward to be disengaged from the needle 70. The sample metering chambers 21a to 21d do not need to have the same volume, and in accordance with the respective measurement subjects, their volumes are so determined as to provide subsequent appropriate dilution degrees, respectively.

Blood sensors 52, 53, 54 and 55 detect the leading end of the flow of the blood sample. In accordance with a detection signal from these blood sensors, the suction operation of the sample suction device 170 can be stopped. The operator can designate from a control panel which blood sensor should be used for stopping the operation. In the case of filling the blood sample in all of the four sample metering chambers, when the leading end of the blood reaches the blood sensor 55, the suction of the blood is stopped. In the case of filling the blood sample in two (21d and 21c) of the sample metering chambers, the blood suction is stopped when the leading end of the blood reaches the blood sensor 53. The sample for classifying the leukocytes is collected in the sample metering chamber 21a, the sample for counting the leukocytes is collected in the sample metering chamber 21c, the sample for measuring the reticulocytes is collected in the sample metering chamber 21b, and the sample for counting the erythrocytes is collected in the sample metering chamber 21d.

(b) Reagent suction step

After the sample metering chambers 21a to 21d are stopped at the reagent suction step region as a result of the intermittent rotation of the rotary sliding member 20, the whole blood sample in the sample metering chamber 21a is introduced into the leukocyte staining chamber 29 via the connecting pipe 68a, the whole blood sample in the sample metering chamber 21b is introduced into the reticulocyte staining chamber 30 via the connecting pipe 68b, the sample in the sample metering chamber 21c is introduced into the erythrocyte hemolysis chamber 25 via the connecting pipe 68c, and the sample in the sample metering chamber 21d is introduced into the erythrocyte dilution chamber 26 via the connecting pipe 68d. These chambers 25, 26, 29 and 30 are called the mixing chambers as described above. The leukocyte cell staining liquid, the reticulocyte staining liquid, the hemolysis agent-containing liquid and the dilution liquid are introduced from the reagent liquid supply device 171 respectively into the leukocyte staining chamber 29, the reticulocyte staining chamber 30, the erythrocyte hemolysis chamber 25 and the erythrocyte dilution chamber 26.

The operations of the apparatus in the reagent suction step, the agitating step and the divided pouring step are the same, and therefore the leukocyte staining will be mainly described hereafter with reference to FIGS. 5B, 5C and 5D. When the staining liquid is fed from the reagent discharge port 57 toward the sample metering chamber 21a by the liquid feeding operation of the reagent liquid supply device 171, the blood sample band in the sample metering chamber 21a is introduced into the mixing chamber 29, and part of the staining liquid extruding the blood sample is also subsequently introduced into the mixing chamber 29. Since the connecting pipe 68 and the mixing chamber 29 are filled beforehand with the staining liquid, the blood sample band is introduced into the mixing chamber 29 in such a manner that the opposite ends of the blood sample band are kept in contact with the staining liquids, respectively. At the time when the blood sample band is completely introduced into the mixing chamber 29, the liquid feeding operation by the reagent liquid supply device 171 is stopped. As a result, the blood sample and the staining liquid reagent are received in the mixing chamber 29 (which is greater in volume than the sample metering chamber) in a predetermined volume ratio.

(c) Agitating step

When the rotary sliding member 20 is further intermittently rotated by two steps, the mixing chamber 29 containing the blood sample and the staining liquid is brought into a condition shown in FIG. 5C. Namely, the mixing chamber 29 communicates at its upper portion with the mixture liquid releasing pipe 59, and at its lower portion with the discharge pipe 60. In this condition, the liquid advancing-retracting device 175 is operated to advance (move upward) and retract (move downward) the mixture liquid in the mixing chamber 29. During the advancing movement of the liquid, the upper end surface of the mixture liquid is introduced into the port 209, and during the retracting movement, the lower end surface of the mixture liquid is introduced into the port 208. This reciprocal movement of the liquid is continued until the blood sample and the staining liquid are sufficiently agitated and mixed together.

In the construction shown in FIG. 5C, the port 208 and the port 209 are out of alignment with each other, that is, their centerlines or axes do not coincide with each other. With this arrangement, the reciprocally-moved liquid can better impinge on the upper and lower wall surfaces to produce a turbulence in the mixing chamber 29, thereby enhancing the agitating efficiency. Preferably, a fluid material which will not be dissolved in the mixture liquid and will not affect the staining should be received in the discharge pipe 60. Instead of such a fluid material, an air gap may be interposed between the mixture liquid and the syringe liquid.

(d) Divided pouring

When the rotary sliding member 20 is further intermittently rotated by two steps, the mixing chamber 29 containing the agitated mixture liquid is brought into a position shown in FIG. 5D. The extrusion device 172 feeds a predetermined amount of the extrusion liquid, so that the mixture liquid, containing the leukocytes which are being stained in the mixing chamber 29, is fed via the connecting pipe 69 toward the discharge pipe 62a. As a result, the mixture liquid of a volume necessary for the measurement is filled in the measurement liquid extracting chamber 31.

(e) Measurement step

When the rotary sliding member 20 is further intermittently rotated by two steps, the measurement liquid extracting chamber 31 is brought into registry with the port 215 to which the sheath flow cell 42 is connected, as shown in FIG. 5E. The blood sample (which is to be used for the measurement) received in the measurement liquid extracting chamber 31 is extruded via the discharge port 63 toward the flow cell 42 by the liquid fed from the measurement liquid introducing device 174. The discharge rate of the blood sample at this time is suitably predetermined in accordance with the concentration of the blood corpuscles to be measured.

The blood, discharged from the sample discharge portion 49 within the flow cell 42, is sheathed by the sheath liquid supplied from the sheath liquid feed device 173, and therefore the blood flows without being in contact with the side wall of the flow cell 42, and stably flows along the centerline of the flow cell 42. The blood corpuscle information with respect to the blood corpuscles in the sample flowing through the flow cell 42 is measured by a photometer or an electrical resistivity measurement device later described.

Figure 12:
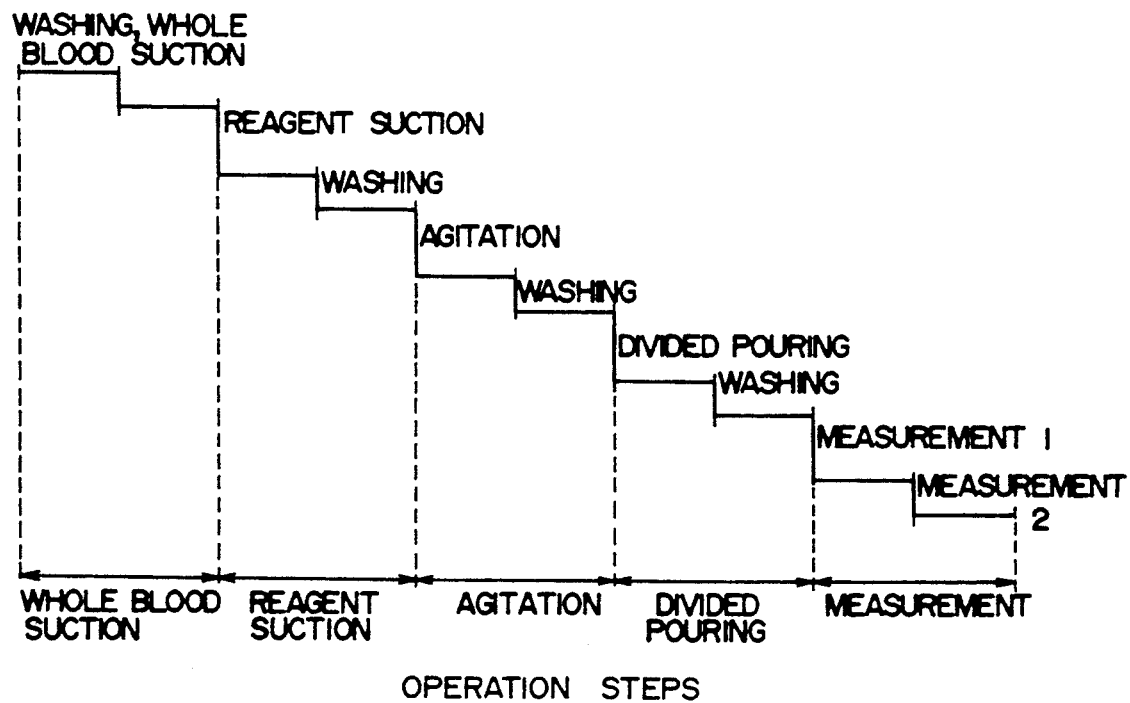
FIG. 12 is a time chart of the operation of the cell analysis apparatus according to the invention.

In this cell analysis apparatus, the two-step intermittent feed is used for each of the reagent suction region, the agitating region and the divided pouring region, as shown in FIG. 12. In the first step of these two steps, the above-mentioned operation is carried out, and in the next step, the chamber used is washed. The washing of the chambers is carried out using the washing holes 90, 91, 92 and 93 (shown in FIGS. 2 and 4) and connecting pipes (not shown). For example, in the reagent suction region, the reagent for the next blood sample is filled in the connecting pipe 68 and the reagent discharge port 57.

Figure 7:
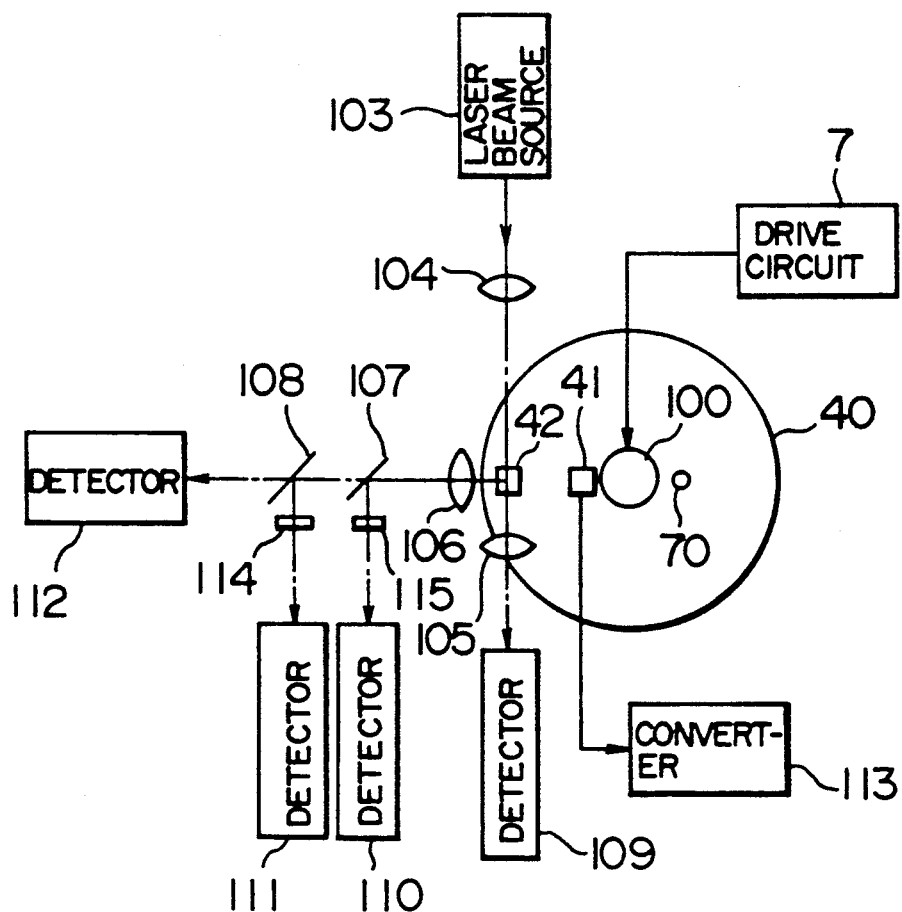
FIG. 7 is a schematic explanatory view of a measurement system of the first embodiment.
Figure 8:
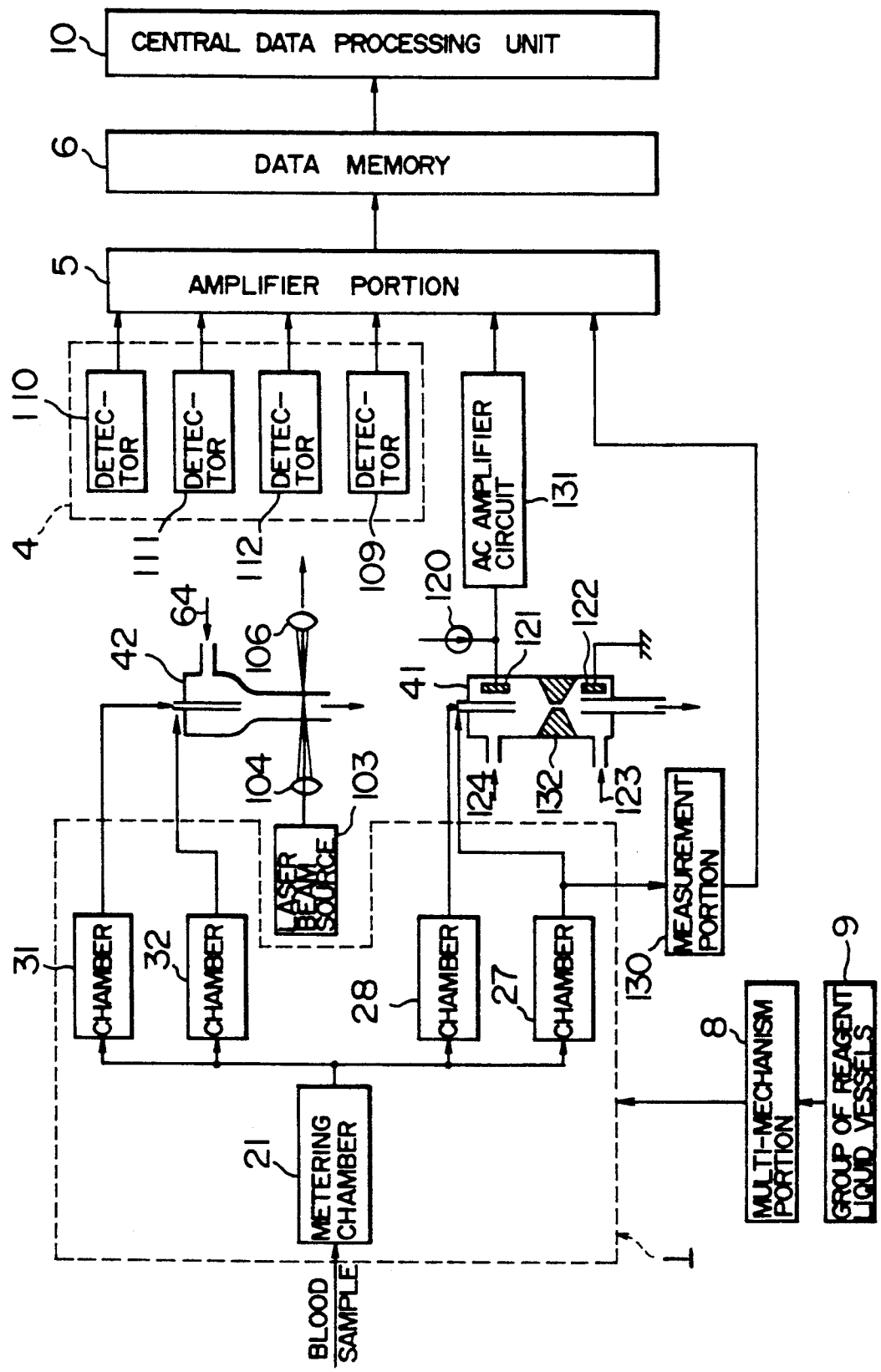
FIG. 8 is an explanatory view of the operation of flow cells in the measurement system.

FIG. 7 shows a general construction of the measurement system of the cell analysis apparatus of FIG. 1, and FIG. 8 is a view of this measurement system, mainly showing the flow cells.

As the laser of the laser beam source 103, there can be used an argon-ion laser, a semiconductor laser, a YAG (yttrium aluminum garnet) laser for producing a second harmonic wave, a helium-neon laser, a helium-cadmium laser, or the like.

In the analysis apparatus of FIG. 1, the argon-ion laser beam source is used to provide a laser beam having a wavelength of 488 nm. The laser beam emitted from the beam source 103 is converged into a very small spot by a condenser lens 104, and is focused on the narrow flow of the blood sample in the flow cell 42. The blood corpuscles emerging in the sample flow pass through the spot area of the applied beam. In the case where the blood corpuscles are the leukocytes stained by acridine orange, they generate fluorescence in response to the radiation of the laser beam, and also generate scattering light.

The forward scattering light is condensed by a condenser lens 105, and is detected by a forward scattering light-detecting photoelectric detector 109, and is converted into an electrical signal. The fluorescence and the side-way scattering light produced by the blood corpuscle are condensed by a condenser lens 106, and are directed toward two beam splitters 107 and 108. With respect to the resulting fluorescence, the lights reflected by the beam splitters 107 and 108 are passed respectively through interference filters 114 and 115 to extract wavelength components necessary for the analysis, and these are detected respectively by photoelectric detectors 110 and 111 and converted into respective electrical signals. The detectors 110 and 111 detect the monochromatic lights of closely-different wavelengths, respectively, so as to effect the two-wavelength light measurement. On the other hand, the side-way scattering light passes through the beam splitters 107 and 108, and is detected by a side-way scattering light-detecting photoelectric detector 112.

The flow cell 41 of another type as shown in FIG. 8 is connected to the upper fixed portion 40 on the rotary sliding member 20, and is disposed closer to the axis of rotation of the rotary sliding member 20 than the fluorescence-measuring flow cell 42 is. In the flow cell 41, a pair of electrodes 121 and 122, disposed respectively on opposite sides of a very small orifice 132, detect a change in electrical resistivity when the blood corpuscle passes through the orifice 132. A converter 113, having a constant current source 120 and an AC amplifier circuit 131, feeds an electrical signal, corresponding to the volume of the blood corpuscle particle passing through the orifice, to the amplifier portion 5.

The blood samples, introduced respectively into the four sample metering chambers 21a to 21d in the rotary sliding member 20, are mixed with the reagent and agitated, and then are fed respectively to the corresponding measurement liquid extracting chambers 31, 32, 27 and 28 for their respective measurement purposes. The blood sample (which contains the stained leukocytes) in the extracting chamber 31 and the blood sample (which contains the stained reticulocytes) in the extracting chamber 32 are fed to the fluorescence-measuring flow cell 42; however, the timings at which the extracting chambers 31 and 32 are brought into registry with the flow cell 42 are different. Namely, the extracting chamber 31 is brought into registry with the flow cell 42 by the first feed step, and the extracting chamber 32 is brought into registry with the flow cell 42 by the next feed step. The blood sample (which contains the erythrocyte hemolysis agent and the undissolved leukocytes) in the measurement liquid extracting chamber 27 is fed to the flow cell 41 after the positioning by the first step is effected, and the diluted blood sample (which contains the erythrocytes) in the extracting chamber 28 is fed to the flow cell 41 after the positioning by the next step is effected, and the particles are counted by the flow cell 41.

As shown in FIG. 8, the sheath liquid supplied from the sheath liquid supply device 173 is introduced into the flow cell 41 from feed inlets 123 and 124. The sheath liquid from the feed inlet 123 rapidly discharges the blood corpuscles, which have passed through the orifice 132, from the flow cell. The sheath liquid to be supplied to the flow cells 41 and 42 is composed of a physiological salt solution. A constant electric current is caused by the constant current source 120 to flow between the electrodes 121 and 122 within the flow cell 41. When the blood corpuscle passes through the very small orifice 132, the electrical resistivity is increased to increase the voltage between the electrodes. This voltage change is proportional to the volume of the passing blood corpuscle.

The leukocyte-counting blood sample to be introduced into the measurement liquid extracting chamber 27 is prepared by mixing and agitating the whole blood sample and the hemolysis agent-containing liquid in the hemolysis chamber 25. Part of the blood sample in the extracting chamber 27 is led to a hemoglobin measurement portion 130, and the erythrocyte hemoglobin concentration based on the erythrocyte hemolysis is measured. The erythrocyte-counting blood sample to be introduced into the measurement extracting chamber 28 is prepared by mixing and agitating the whole blood sample and the dilution liquid in the dilution chamber 26. The erythrocytes and the blood platelets in the sample from the extracting chamber 28 are counted by the flow cell 41.

The reticulocyte-measuring blood sample is introduced into the measurement liquid extracting chamber 32 from the reticulocyte staining chamber 30. The reticulocyte is part or residue of RNA (ribonucleic acid) related to the synthesis of the hemoglobin in the erythrocyte, and thus is an examination item for knowing the erythrocyte productivity. In this embodiment, the fluorescent staining is made by acridine orange, and the fluorescence intensity is measured by the flow cell 42. As the fluorescent staining agent, auramine 0, thiazole orange, or the like may be used.

Figure 10:
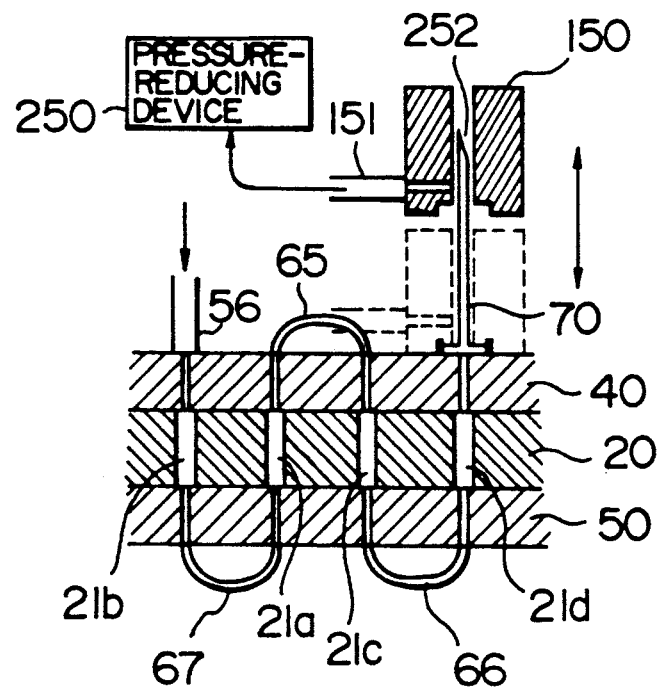
FIG. 10 is an explanatory view of a needle block in the first embodiment

FIG. 10 is a view showing the function of washing the piercing needle 70 attached to the upper fixed portion 40 of the cell analysis apparatus of FIG. 1. The inner and outer surfaces of the blood thief tube-piercing needle 70 are washed by a needle-washing block 150, thereby reducing mutual contamination between the samples. A discharge port 151 of the washing block 150 is connected to a pressure-reducing device 250 having a vacuum pump, and the discharge liquid in the flow passage, as well as the ambient air, is drawn by the pressure-reducing device 250.

At the time of the sampling, the washing block 150 is moved upward to a level above the distal end of the needle 70 so as not to interfere with the attachment of the blood thief tube 51, and is further moved horizontally to stand by. At the time of the washing, the washing block 150 is returned to the position of the needle 70, and is further moved downward to the upper surface of the upper fixed portion 40, so that the needle 70 is inserted into an insertion hole 252 formed in the central portion of this washing block. These mechanisms are mounted on the base 183.

The needle 70 is washed simultaneously with the sample metering chambers 21a to 21d and the connecting pipes 65, 66 and 67. The washing liquid supplied from the sample suction device 170 is introduced from the conduit 56, and passes through the metering chambers and the connecting pipes, which are connected together in series, and is discharged from the needle 70. The washing liquid discharged from the distal end of the needle 70 is drawn into the discharge port 151, and is removed. During the time when the washing liquid flows from the distal end of the needle 70, the outer surface of the needle 70 is washed by reciprocally moving the washing block 150 upward and downward.

Figure 11:
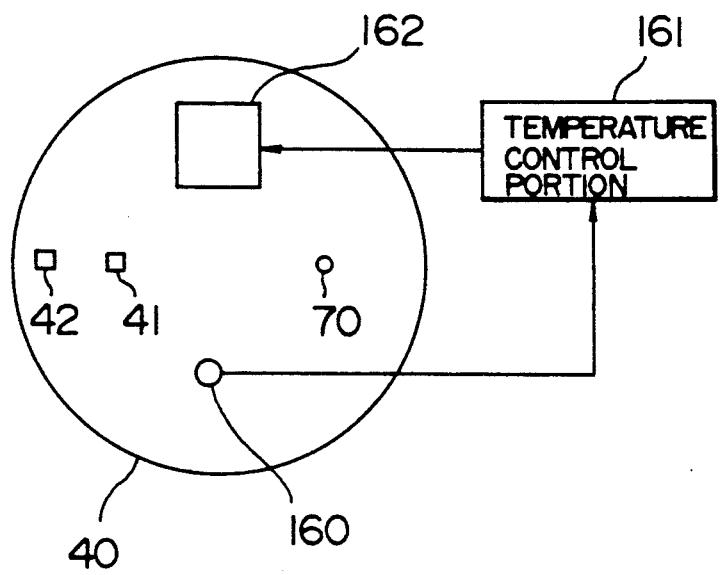
FIG. 11 is an explanatory view of a temperature control system in the first embodiment.

FIG. 11 is a view for explaining a temperature control system of the cell analysis apparatus of FIG. 1. The rotary sliding member 20 and the upper and lower fixed portions 40 and 50 of the pretreatment portion 1 are made of alumina which is a ceramic of good thermal conductivity. A heating portion 162 having a heating element embedded therein, as well as a temperature sensor portion 160 for detecting the temperature of the pretreatment portion 1, are mounted on the upper fixed portion 40. By comparing the temperature, detected by the temperature sensor portion 160, with a temperature set in a temperature control portion 161, the heating portion 162 is controlled to be turned on and off so as to maintain the pretreatment portion 1 at a predetermined temperature, for example, of 40° C.

The degree of staining of the blood corpuscles is influenced by the temperature, and therefore in order to maintain the whole of the pretreatment portion 1 at the same temperature, the upper and lower fixed portions 40 and 50 are held in contact with the rotary sliding member 20, and preferably each of these parts should be constituted by a unitary member. A plurality of heating portions 162 and a plurality of temperature sensor portions 160 may be provided at the pretreatment portion 1. In such a case, they may be provided in the upper and lower fixed portions.

Next, a second embodiment of the present invention will be described with reference to FIGS. 13 to 16. A cell analysis apparatus of this second embodiment is similar to that of the first embodiment in a method of mixing and agitating a blood sample and a reagent, and also in a method of measuring blood corpuscle information by a flow cell. Therefore, explanation thereof will be omitted. The second embodiment differs from the first embodiment in the manner of feeding the blood sample to the flow cell after the blood sample is mixed with the reagent and is agitated. Features of the second embodiment will be described hereafter.

Figure 13:
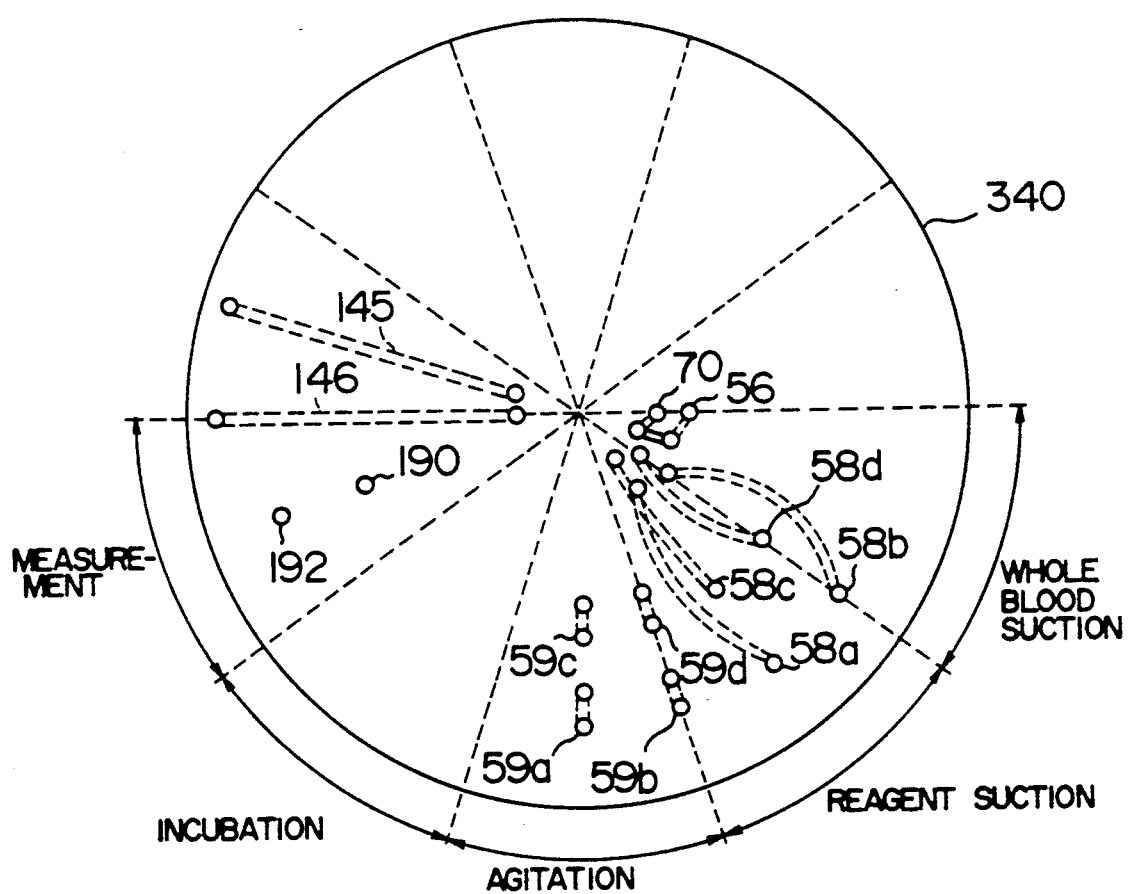
FIG. 13 is an explanatory view of a fixed portion of a second embodiment of the invention.
Figure 14:
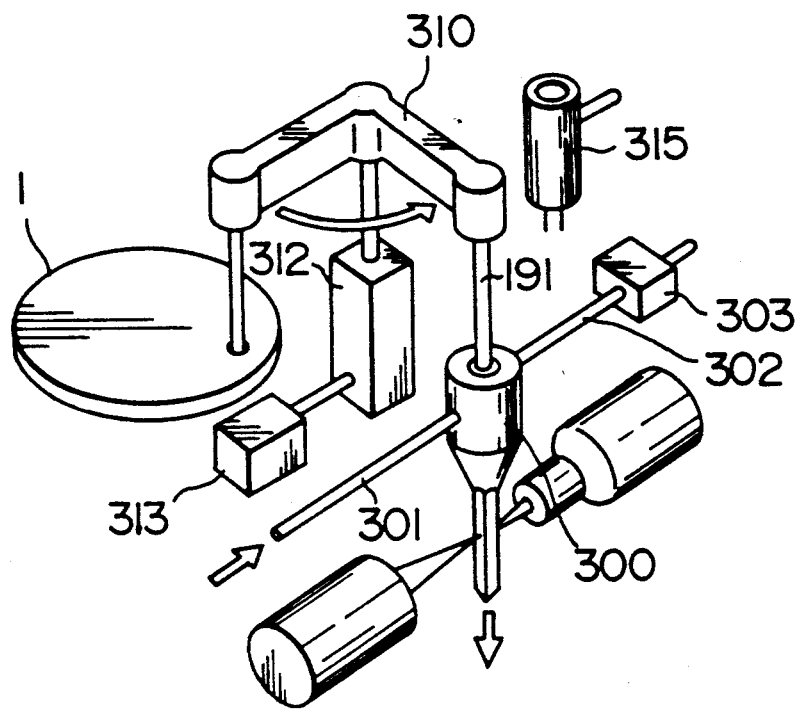
FIG. 14 is a view showing a general construction of a measurement liquid pipetter in the second embodiment.
Figure 15:
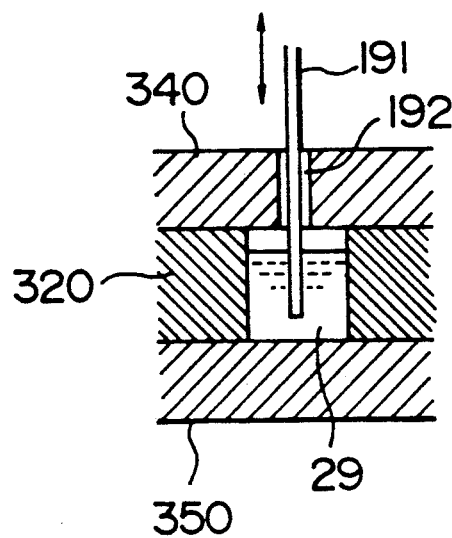
FIG. 15 is an explanatory view of the measurement liquid suction by the measurement liquid pipetter.
Figure 16:
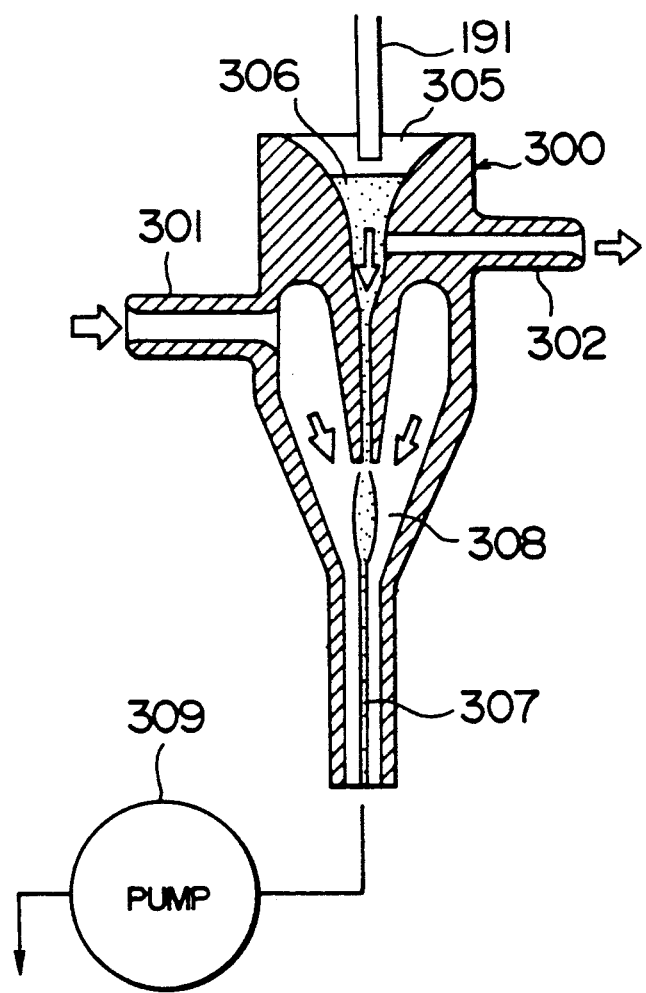
FIG. 16 is an explanatory view of divided pouring to a flow cell by the measurement liquid pipetter.

In FIGS. 13 to 16, a pretreatment portion 1 comprises a rotary sliding member 320, an upper fixed portion 340 and a lower fixed portion 350, as best shown in FIG. 15. As shown in FIG. 13, in addition to discharge pipes 58a to 58d, mixture liquid releasing pipes 59a to 59d etc., and holes 190 and 192 are provided in the upper fixed portion 340. As shown in FIG. 15, a pipetting probe 191 mounted on a movable arm 310 (FIG. 14) is inserted through the hole 192 into a mixing chamber 29, and draws a predetermined amount of a measurement mixture liquid, and discharges this measurement liquid to a flow cell inlet 305 (FIG. 16) of a flow cell 300. In the pretreatment portion 1, an incubation region is provided between an agitating region and a measurement region so that a sufficient time for staining the blood corpuscles can be obtained.

The flow cell 300 has an inlet 301 for supplying a sheath liquid, and an excess sample discharge tube 302. An on-off valve 303 is provided in the discharge tube 302. The downstream side of the flow cell 300 is connected to a liquid feed pump 309. The pipetting probe 191 is moved upward and downward and is swung by a drive mechanism 312. The probe 191 communicates with a suction discharge pump 313.

After the probe 191 discharges the blood sample, extracted from the mixing chamber 29, to the flow cell inlet 305, the probe 191 is further swung to a washing vessel 315 where its outer and inner surfaces are washed, and then the probe 191 is returned to the position of the hole 192. The sample 306 discharged to the flow cell 300 forms a sample flow 307 at a central portion of a sheath liquid flow 308, and the fluorescence and the scattering light based on the blood corpuscles in the sample are then measured.

Figure 17:
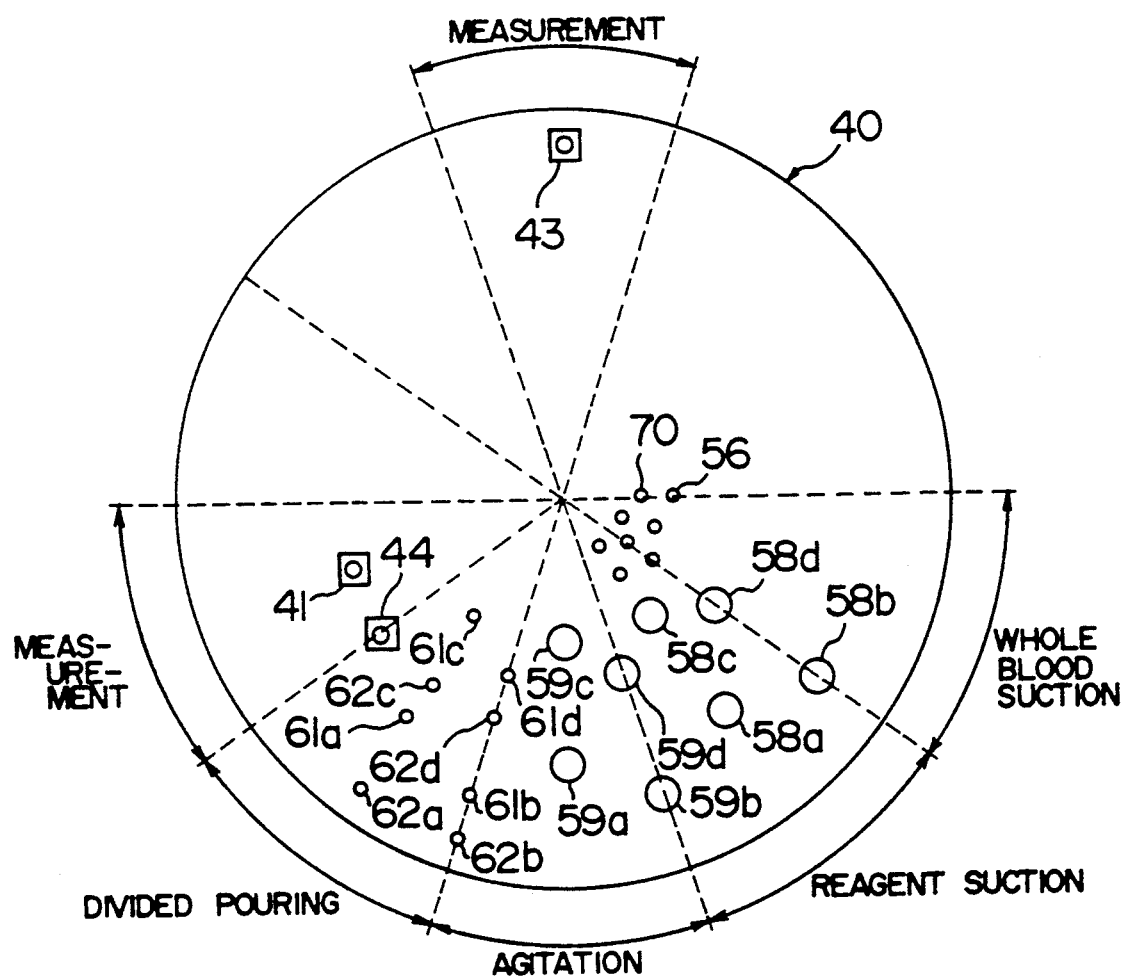
FIG. 17 is an explanatory view of fixed portion of a third embodiment of the invention.

FIGS. 17, 18A and 18B are views for explaining a third embodiment of the present invention. In FIG. 17, an upper fixed portion 40 of a pretreatment portion 1 of this embodiment is largely similar to that of the analysis apparatus of FIG. 1, but the positions of the flow cells are different. For a measurement item in which the whole blood is merely diluted so as to count the blood corpuscles, a flow cell 41 is used so that the measurement can be started a relatively short time after the agitation. For effecting a fluorescent measurement after staining the blood corpuscles, there is used a flow cell 43 to which the blood sample reaches a long time after the mixing of the staining liquid. Thus, a plurality of items of different treatment times can be dealt with and measured in a parallel manner.

A plurality of flow cells 41 and 44 are provided on a common circle having the center disposed at an axis of rotation of a rotary sliding member. The flow cell 44 is of an electrical resistivity measurement type. Even if the pretreatment portion has two lines of treatment chambers, the two measurements can be simultaneously effected at the time of the same feed step. For example, the counting of the leukocytes can be effected by the flow cell 41, and the counting of the erythrocytes can be effected by the flow cell 44.

In FIG. 18, there is shown a measurement liquid extracting chamber suitable for reducing the influence of the diffusion in the flow passage of the blood sample. In this modified form, the measurement liquid extracting chamber formed in the rotary sliding member 20 has a chamber 31 and a chamber 84, and these two chambers communicate with each other by a narrow connecting passage 80. For shifting the blood sample from a mixing chamber 29 to the measurement liquid extracting chamber, the blood sample is fed via a connecting pipe 82 toward a conduit 85, as shown in FIG. 18A. For feeding the extracted blood sample to the flow cell 41, an extrusion liquid is supplied via the conduit 85, as shown in FIG. 18B. In this case, since the blood sample exists in that portion of the conduit 85 close to the upper fixed portion 40, the sample in the measurement liquid extracting chambers 31 and 84 is prevented from being diffused into the extrusion liquid. This method is effective particularly when counting the number of the blood corpuscles.

Next, reference is made to an example of an experiment in which the leukocyte classifying measurement was conducted using the cell analysis apparatus of FIG. 1. During the reagent suction step, the acridine orange staining agent liquid was introduced into the mixing chamber, and the fluorescence was detected 60 seconds after the mixing and agitation were completed. The applied beam was an argon laser beam with a wavelength of 488 nm. The fluorescences (to be detected) from the stained leukocyte were a green fluorescence with a wavelength of around 530 nm and a red fluorescence with a wavelength of not less than 630 nm.

FIG. 19 shows a two-dimensional scatter diagram of the fluorescence signal. In FIG. 19, the abscissa axis represents the red fluorescence intensity, the ordinate axis represents the green fluorescence intensity, and each of the plotted points represents one leukocyte. The leukocyte distribution is divided into five clusters, and the leukocytes are classified into the neutrophilic leukocyte, the eosinophilic leukocyte, the basophilic leukocyte, the monocyte and the lymphocyte.

Figure 20:
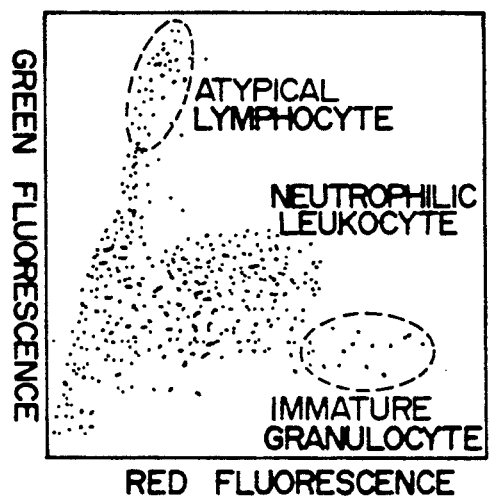
FIG. 20 is a view showing a measurement example of a blood sample in which abnormal leukocytes exist.

FIG. 20 shows a two-dimensional scatter diagram with respect to the blood sample in which the immature granulocytes and the atypical lymphocytes are present. In FIG. 20, the indication is made with the sensitivity of the photo-detecting system lowered. As is clear form the drawings, the immature granulocytes appear at the right side of the neutrophilic leukocytes and the eosinophilic leukocytes, and the atypical lymphocytes appear at the upper side of the lymphocytes. The number of the immature granulocytes, the number of the atypical lymphocytes, and the differential ratios thereof are determined through data processing by the central data processing unit 10.

Figure 21:
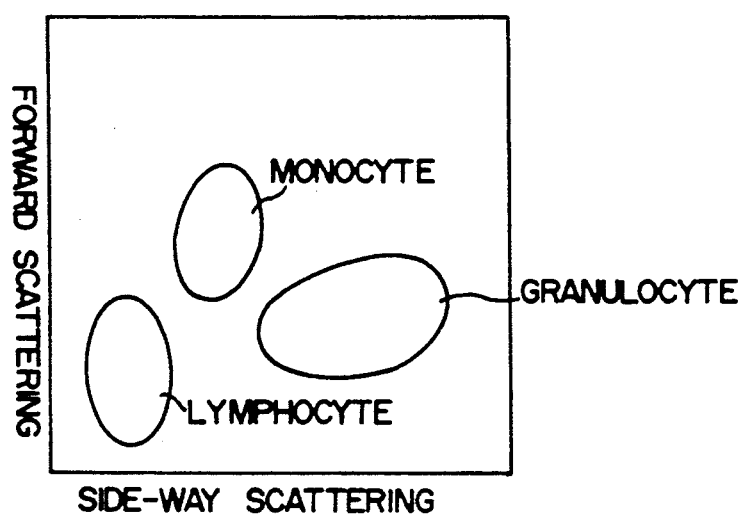
FIG. 21 is a scatter diagram of light scattering.

FIG. 21 is a scatter diagram of the light scattering by the leukocytes. The abscissa axis represents the sideway scattering light intensity, and the ordinate axis represents the forward low-angle scattering light intensity. The hemolysis treatment of the erythrocytes by saponin enables the light scattering measurement with respect to the leukocytes. The leukocytes are divided into three clusters, and are classified into the lymphocytes, the monocytes and the granulocytes. The basophilic leukocytes exist in overlapping relation to the lymphocytes. In the scatter diagram of the light scattering, the cluster separation between the lymphocytes and the monocytes is good. Therefore, by combining the acridine orange fluorescent staining method with the light scattering method, the precision of the classification of the leukocytes can be enhanced.

As described above, in the present invention, the sample pretreatment portion is constituted by the rotary sliding member and the fixed portions, and the sample and the reagent can be mixed together in this pretreatment portion. Therefore, the length of the flow passage of the pretreatment system can be shortened, and the analysis apparatus can be of a smaller size.

What is claimed is:

1. A cell analysis apparatus for effecting multiple types of sample treatments to multiple samples, comprising:
   a rotor radially divided equally into a plurality of segments of the same angle, each of said segments having a plurality of chambers therein of identical construction;
   a pair of stators sandwiching said rotor;
   means for providing each of a plurality of different samples to a chamber of a different one of the segments;
   means for intermittently rotating the rotor through an angle corresponding to one-half of one segment to bring a sample in a segment to a treatment position corresponding to a position on one of said stators; and
   means for performing one of a plurality of different sample treatments for each of the plurality of different samples, including means for performing a first sample treatment and thereafter performing a second sample treatment different from the first sample treatment following each angular rotation of the rotor.

2. A cell analysis apparatus according to claim 1, in which said plurality of different sample treatments includes at least one of the group consisting of sample suction, divided pouring, dilution, staining, agitation, measurement of sample parameters and washing.

3. A cell analysis apparatus according to claim 2, wherein the sample providing means includes sample suction means for receiving a sample by suction and for delivering a sample to one of the chambers in said segments, said sample suction means being directly provided on one of said stators.

4. A cell analysis apparatus according to claim 2, further comprising a sample measuring position, directly provided on one of said stators, at which a sample parameter of a sample drawn from one of said rotor segment chambers is measured.

5. A cell analysis apparatus according to claim 4, further comprising a plurality of sample measuring positions, directly provided on said one stator, at which different sample treatments are respectively performed on respective samples drawn from respective rotor segment chambers.

6. A cell analysis apparatus according to claim 5, wherein at least one of said sample measurement positions is located a distance in a rotational direction from another of said measuring positions, said distance corresponding to a reaction time of a treatment, when reaction times are different for different sample treatments.

7. A cell analysis apparatus according to claim 2, wherein said chambers include a dilution chamber and a divided pouring chamber, and said apparatus further comprises a quantitative analysis flow cell operably associated with one of the stators for receiving a sample from one of the rotor segment chambers, said dilution chamber having a volume that is larger than the volume of the divided pouring chamber and the quantitative analysis flow cell.

8. A cell analysis apparatus according to claim 1, in which the locations of said plurality of chambers in the segments correspond to treating portions in which said plurality of sample treatments are to be effected, so that said samples are shifted from one of said chambers to another of said chambers within the same segment with each angular rotation of the rotor of a predetermined angle in a predetermined direction.

9. A cell analysis apparatus according to claim 1, further comprising a plurality of sample measuring positions, directly provided on one of said stators, at which different sample treatments are respectively performed on respective samples drawn from respective rotor segment chambers, wherein at least one of said sample measuring positions is located a distance in a rotational direction from another of said measuring positions, said distance corresponding to a reaction time of a treatment, when sample reaction times are different for different sample treatments.

10. A cell analysis apparatus according to claim 1, wherein at least one segment includes a first portion and a second portion, and further comprising means for providing a sample treatment to a sample contained in a chamber located in the first portion of said at least one segment at a treatment position and means for washing a chamber located in the second portion of said at least one segment at a washing position while said first position is at said treatment position.

11. A cell analysis apparatus according to claim 1, wherein at least one segment includes a first portion and a second portion, and further comprising means for simultaneously performing a different analysis for each of a sample contained in a chamber located in the first portion of said at least one segment at a first treatment position, and a sample contained in a chamber located in the second portion of said at least one segment at a second treatment position while said first portion is at said first treatment position.

12. A method of cell analysis for effecting multiple kinds of sample treatments to a sample by rotating a rotor sandwiched by two stators so as to change the sample treatments, comprising the steps of:
   providing a rotor that is radially divided equally into a plurality of segments of the same angle, each of said segments having a plurality of chambers therein of identical construction;
   providing a plurality of different samples, one sample to a respective chamber of one of said equally divided segments;
   performing one of a plurality of different sample treatments for each of the plurality of different samples; and
   intermittently rotating said rotor through an angle corresponding to one-half of one segment;
   wherein said plurality of sample treatments are changed with each angular rotation of the rotor.

13. A method of cell analysis according to claim 12, wherein each of said plurality of different samples is a blood sample.

14. A method of cell analysis according to claim 12, in which said plurality of different sample treatments include at least one from the group consisting of blood corpuscle counting, leukocyte classifying, and reticulocyte counting.

* * * * *